United States Patent [19]

Sayo et al.

[11] Patent Number: 5,066,815

[45] Date of Patent: Nov. 19, 1991

[54] PROCESS FOR PREPARING OPTICALLY ACTIVE ALCOHOL

[75] Inventors: Noboru Sayo; Hidenori Kumobayashi; Susumo Akutagawa, all of Kanagawa; Ryoji Noyori; Hidemasa Takaya, both of Aichi, all of Japan

[73] Assignee: Takasago International Corporation, Tokyo, Japan

[21] Appl. No.: 520,149

[22] Filed: May 8, 1990

Related U.S. Application Data

[63] Continuation of Ser. No. 207,476, Jun. 16, 1988, abandoned.

[30] Foreign Application Priority Data

Jun. 19, 1987 [JP] Japan ................. 62-152483

[51] Int. Cl.$^5$ ............................. C07D 307/33
[52] U.S. Cl. .................... 549/319; 549/325;
502/213; 560/60; 562/470; 562/579; 564/503;
568/561; 568/668; 568/678; 568/807; 568/811;
568/812; 568/833; 568/838
[58] Field of Search ............. 549/319, 325; 502/213;
560/60; 562/579, 470; 564/503; 568/861, 862,
811, 812, 833, 838, 841, 561, 668, 678, 807;
558/252

[56] References Cited

U.S. PATENT DOCUMENTS

| | | | |
|---|---|---|---|
| 3,957,827 | 5/1976 | Lyons | 549/325 |
| 4,739,084 | 4/1988 | Takaya et al. | 556/21 |
| 4,739,085 | 4/1988 | Takaya et al. | 556/21 |
| 4,933,482 | 6/1990 | Sayo et al. | 558/252 |

FOREIGN PATENT DOCUMENTS 0174057  3/1986  European Pat. Off. .

OTHER PUBLICATIONS

Hayashi et al., "Tetrahedron Letters", No. 48, pp. 4351 & 4354, 1976, Pergamon Press, Great Britain.
Ikariya et al., J. Chem. Soc., Chem. Commun., pp. 922–924, 1985.
Journal of the American Chemical Society, vol. 109, No. 5, Mar. 4, 1987, pp. 1596 and 1597, American Chemical Society, Wash. DC, US; H. Takaya et al., "Enantioselective Hydrogenation of Allyic and Homoallylic Alcohols".
Journal of the American Chemical Society, vol. 108, No. 22, 29th Oct. 1986, pp. 7117–7119, American Chemical Society, Wash. DC, US; R. Noyori et al., "Asymmetric Synthesis of Isoquinoline Alkaloids by Homogeneoous Catalysts".
Journal of Organometallic Chemistry, vol. 198, No. 1, 1980, pp. 73–80, Elsevier Sequvia S. A. Lausanne, Ch. M. Bianchi et al. "Asymmetric Synthesis by Chiral Ruthenium Complexes".
Journal of the American Chemical Society, vol. 109, No. 19, Sep. 1987, pp. 5856–5858.
Journal of the American Chemical Society, vol. 110, No. 2, Jan. 20, 1980, pp. 629–631.

Primary Examiner—C. Warren Ivy
Assistant Examiner—Ba K. Trinh
Attorney, Agent, or Firm—Sughrue, Mion, Zinn, Macpeak & Seas

[57] ABSTRACT

A process for preparing an optically active alcohol is disclosed, which comprises asymmetrically hydrogenating a carbonyl compound in the presence of a ruthenium-optically active phosphine complex as a catalyst. The resulting alcohol has high optical purity.

2 Claims, No Drawings

PROCESS FOR PREPARING OPTICALLY ACTIVE ALCOHOL

This is a continuation of application Ser. No. 07/207,476 filed June 16, 1988 now abandoned.

FIELD OF THE INVENTION

This invention relates to a process for preparing an optically active alcohol by asymmetric hydrogenation of a carbonyl compound in the presence of a ruthenium-optically active phosphine complex as a catalyst. The optically active alcohol obtained by the process is useful as an intermediate for synthesizing naturally-occurring substances, a chiral moiety of a ferroelectric liquid crystal, or an intermediate of pharmaceuticals.

BACKGROUND OF THE INVENTION

Processes for synthesizing optically active alcohols by asymmetric hydrogenation of carbonyl compounds have hitherto been reported. For example, Y. Ohgo proposed asymmetric hydrogenation using bis(dimethylglyoxymato)cobalt (II)-quinine as a catalyst as described in *Chem. Lett.*, 709–712 (1974). However, this process attains such poor results as 2.5 to 73%ee in optical yield of the resulting alcohol and 10 to 20 in a substrate/catalyst molar ratio.

It has been also been proposed to use a rhodium-optically active phosphine as a catalyst as disclosed, e.g., in I. Ojima et al., *J.C.S. Chem. Commu.*, 428–430 (1977) and T. Hayashi et al., *Tetrahedron Lett.*, No. 48, 4351–4354 (1976).

According to the process using the cobalt-optically active amine, not only the alcohol produced has low optical purity but the catalytic activity is not sufficient.

Further, in the process of using the rhodium-optically active phosphine, metallic rhodium to be used in the catalyst is expensive due to limitations in place and quantity of production. When used as a catalyst component, it forms a large proportion in cost of the catalyst, ultimately leading to an increased cost of the final commercial products.

SUMMARY OF THE INVENTION

As a result of extensive investigations with the purpose of settling the above-described problems, the inventors have found that an optically active alcohol having high optical purity can be obtained efficiently by asymmetric hydrogenation of a carbonyl compound in the presence of a relatively cheap ruthenium-optically active phosphine complex as a catalyst. The present invention has been completed based on this finding.

The present invention relates to a process for preparing an optically active alcohol represented by formula (I):

(I)

wherein A represents a lower alkyl group (the alkyl moiety thererof perferably has from 1 to 4 carbon atoms), a lower haloalkyl group (the alkyl moiety thererof perferably has from 1 to 4 carbon atoms), a substituted or unsubstituted phenyl group (examples of the substituent include a halogen atom, a hydroxyl group, and a lower alkoxy group having preferably from 1 to 4 carbon atoms), or a substituted or unsubstituted benzyl group (examples of the substituent include a halogen atom, a hydroxyl group, and a lower alkoxy group having preferably from 1 to 4 carbon atoms); and B represents an acyl group having from 1 to 4 carbon atoms, a lower alkoxycarbonyl group (the alkyl moiety thererof perferably has from 1 to 4 carbon atoms), a haloalkyl group (the alkyl moiety thererof perferably has from 1 to 4 carbon atoms), a hydroxycarbonyl group, a lower alkoxyalkyl group (the alkyl moiety thererof perferably has from 1 to 4 carbon atoms), a hydroxymethyl group, a substituted or unsubstituted benzoyl group (examples of the substituent include a halogen atom, a hydroxyl group, and a lower alkoxy group having preferably from 1 to 4 carbon atoms), or a lower alkyl-substituted aminomethyl group (the alkyl moiety thererof perferably has from 1 to 4 carbon atoms); or A and B are taken together with the adjacent carbon atom to form a substituted or unsubstituted and carbocyclic or heterocyclic 5- or 6-membered 1,2-diketone, which comprises asymmetrically hydrogenating a carbonyl compound represented by formula (II):

(II)

wherein A and B are as defined above, in the presence of a ruthenium-optically active phosphine complex as a catalyst.

DETAILED DESCRIPTION OF THE INVENTION

The carbonyl compound represented by formula (II) which can be used in the present invention as a starting compound specifically but non-limitingly includes diacetyl, dibenzoyl, cyclopentan-1,2-dione, cyclohexan-1,2-dione, 1-phenyl-1,2-dioxopropane, 1-phenyl-2,3-dioxobutane, phenylglyoxylic acid, 3-methyl-2-oxobutanoic acid, ethyl 3-methyl-2-oxobutanoate, ketopantolactone, ethyl phenylglyoxylate, phenylpyruvic acid, methyl phenylpyruvate, ethyl phenylpyruvate, pyruvic acid, methyl pyruvate, α-chloroacetone, α-bromoacetone, α-chloroacetophenone, 1-chloro-3-phenylacetone, α-dichloroacetone, α-trichloroacetone, 1-chloro-3-dichloroacetone, 1-chloro-3-methyl-2-butanone, α-methylaminoacetone, α-dimethylaminoacetone, α-hydroxyacetone, 1-hydroxy-3-methyl-2-butanone, α-hydroxyacetophenone, 1-hydroxy-3-phenylacetone, α-methoxyacetone, α-methoxyacetophenone, α-ethoxyacetone, α-butoxyacetophenone, p-methoxyphenylpyruvic acid, 3,4-dimethoxyphenylpyruvic acid, 2-oxobutanoic acid, 3,4-dioxohexane, 4,5-dioxooctane, 1-chloro-2-oxobutane, 1,1-fluoro-2-oxobutane, α-dibromoacetone, 1-hydroxy-2-oxobutane, 1-dimethylamino-2-oxobutane, 1-dimethylamino-2-oxopentane, 1-hydroxy-2-oxopentane, 1-hydroxy-2-oxohexane, α-chloro-p-methoxyacetophenone, p-methoxydibenzoyl, 1-hydroxy-2-oxo-3-methylbutane, 1-ethoxy-2-oxobutane, 1-butoxy-2-oxobutane, 1-methylamino-2-oxobutane, 1-butylamino-2-oxopropane, 1-dibutylamino-2-oxopropane, etc.

The ruthenium-optically active phosphine complex to be used as a catalyst includes those represented by the following formulae (III), (V), and (VI):

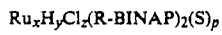
(III)

wherein R-BINAP represents a tertiary phosphine represented by formula (IV): wherein R represents a hydrogen atom, a methyl group, or a t-butyl group; S represents a tertiary amine; when y represents 0, then x represents 2, z represents 4, and p represents 1; and when y represents 1, then x represents 1, z represents 1, and p represents 0.

[RuH$_l$(R-BINAP)$_v$]Y$_w$  (V)

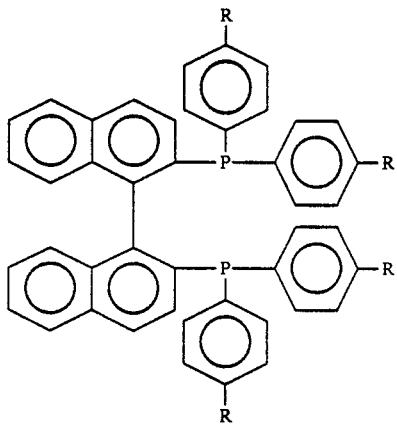

(IV)

wherein R-BINAP is as defined above; Y represents ClO$_4$, BF$_4$, or PF$_6$; when l represents 0, then v represents 1, and w represents 2; and when l represents 1, then v represents 2, and w represents 1.

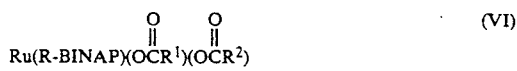

(VI)

wherein R-BINAP is as defined above; and R$^1$ and R$^2$ each represents a lower alkyl group or a trifluoromethyl group.

In the formulae (III) to (VI), "BINAP" represents a 2,2'-bis(diphenylphosphino)-1,1'-binaphthyl moiety (hereinafter the same).

The compound of formula (III) can be obtained by the process disclosed in T. Ikariya et al., *J. Chem. Soc., Chem Commun.*, 922–924 (1985) and Japanese Patent Application (OPI) No. 63690/86 (the term "OPI" as used herein means "unexamined published Japanese patent application"). More specifically, the complex of formula (III) wherein y is 0 can be prepared by reacting 1 mol of [RuCl$_2$(COD)]$_n$ (wherein COD represents cycloocta-1,5-diene, hereinafter the same), which is obtained by reacting ruthenium chloride and COD in an ethanol solution, and 1.2 mols of a 2,2'-bis(di-p-R-phenylphosphino)-1,1'-binaphthyl (R-BINAP) under heating in a solvent, e.g., toluene, ethanol, etc., in the presence of 4 mols of a tertiary amine, e.g., triethylamine. The complex of formula (III) wherein y is 1 can be obtained by reacting 1 mol of [RuCl$_2$(COD)]$_n$, 2.25 mols of R-BINAP, and 4.5 mols of a tertiary amine.

The complex of formula (V) wherein l is 0, v is 1, and w is 2 can be prepared by reacting Ru$_2$Cl$_4$(R-BINAP)$_2$-(NEt$_3$) (wherein Et represents an ethyl group, hereinafter the same), which is obtained by the above-described process, with a salt represented by formula (VII):

MY  (VII)

wherein M represents Na, K, Li, Mg, or Ag; and Y is as defined above, in a solvent system comprising water and methylene chloride in the presence of a quaternary ammonium salt or quaternary phosphonium salt represented by formula (VIII):

R$^3$R$^4$R$^5$R$^6$A'B'  (VIII)

wherein R$^3$, R$^4$, R$^5$, and R$^6$ each represents an alkyl group having from 1 to 16 carbon atoms, a phenyl group, or a benzyl group; A' represents a nitrogen atom or a phosphorus atom; and B' represents a halogen atom, as a phase transfer catalyst. The reaction can be carried out by adding the reactants and the phase transfer catalyst of formula (VIII) to a mixed solvent of water and methylene chloride and stirring the system. The amounts of the salt of formula (VI) and of the phase transfer catalyst of formula (VIII) to be added range from 2 to 10 mols (preferably 5 mols) and from 1/100 to 1/10 mol, respectively, per mol of ruthenium. The reaction sufficiently proceeds by stirring at a temperature of from 5° to 30° C. for a period of from 6 to 18 hours, and usually 12 hours.

Examples of the phase transfer catalyst of formula (VIII) are described in literatures, e.g., W. P. Weder and G. W. Gokel, *Sokan Ido Shokubai* (Japanese translation), 1st Ed., Kagaku Dojinsha (1978). After completion of the reaction, the reaction mixture is allowed to stand still, followed by liquid separation. After the aqueous layer is removed, the methylene chloride solution is washed with water, and methylene chloride is removed by distillation under reduced pressure to obtain the desired compound.

The complex of formula (V) where l is 1, v is 2, and w is 1 can be prepared by reacting RuHCl(R-BINAP)$_2$ obtainable by the process disclosed in Japanese Patent Application (OPI) No. 63690/86 with the salt of formula (VII) in a mixed solvent of water and an organic solvent, e.g., methylene chloride, in the presence of the phase transfer catalyst of formula (VIII). The amounts of the salt of formula (VII) and of the phase transfer catalyst of formula (VIII) range from 2 to 10 mols (preferably 5 mols) and from 1/100 to 1/10 mol, respectively, per mol of ruthenium. This reaction sufficiently proceeds by stirring at a temperature of from 5° to 30° C. for a period of from 6 to 18 hours, and usually 12 hours.

The complex of formula (VI) can be prepared by the process previously proposed by the inventors in European Patent No. 245,959A in which Ru$_2$Cl$_4$(R-BINAP)$_2$(NEt$_3$) is reacted with a carboxylic acid salt in an alcohol solvent, e.g., methanol, ethanol, t-butanol, etc., at a temperature of from about 20° to 110° C. for 3 to 15 hours. After the reaction, the solvent is removed by distillation, and the residue is extracted with a solvent, e.g., diethyl ether, ethanol, etc. The extract is then dried to a solid to obtain a crude complex. Recrystallization of the crude product from ethyl acetate, etc. gives a purified product. The acyloxy group in formula (VI) can be altered by appropriately selecting the kind of the carboxylic acid to be used. For example, when the starting complex is reacted with sodium acetate, there is obtained Ru(R-BINAP)(OCOCH$_3$)$_2$. The complex of formula (VI) containing a trifluoroacetyl group can be obtained by reacting the above-obtained diacetate complex with trifluoroacetic acid in a methylene chloride solvent at about 25° C. for about 12 hours.

Specific examples of the above-described ruthenium-phosphine complex according to the present invention are shown below.

Ru$_2$Cl$_4$(BINAP)$_2$(NEt$_3$)
Ru$_2$Cl$_4$(T-BINAP)$_2$(NEt$_3$)
[T-BINAP represents 2,2'-bis(di-p-tolylphosphino)-1,1'-binaphthyl, hereinafter the same]
Ru$_2$Cl$_4$(t-Bu-BINAP)$_2$(NEt$_3$)
[t-Bu-BINAP represents 2,2'-bis(di-p-t-butylphenylphosphino)-1,1'-binaphthyl, hereinafter the same]
RuHCl(BINAP)$_2$
RuHCl(T-BINAP)$_2$
RuHCl(t-Bu-BINAP)$_2$
[Ru(BINAP)](ClO$_4$)$_2$
[Ru(T-BINAP)](ClO$_4$)$_2$
[Ru(t-Bu-BINAP)](ClO$_4$)$_2$
[Ru(BINAP)](BF$_4$)$_2$
[Ru(T-BINAP)](BF$_4$)$_2$
[Ru(t-Bu-BINAP)](BF$_4$)$_2$
[Ru(BINAP)](PF$_6$)$_2$
[Ru(T-BINAP)](PF$_6$)$_2$
[RuH(BINAP)$_2$]ClO$_4$
[RuH(T-BINAP)$_2$]ClO$_4$
[RuH(BINAP)$_2$]BF$_4$
[RuH(T-BINAP)$_2$]BF$_4$
[RuH(BINAP)$_2$]PF$_6$
[RuH(T-BINAP)$_2$]PF$_6$
Ru(BINAP)(OCOCH$_3$)$_2$
Ru(BINAP)(OCOCF$_3$)$_2$
Ru(T-BINAP)(OCOCH$_3$)$_2$
Ru(BINAP)(OCO-t-Bu)$_2$
(t-Bu represents t-butyl)
Ru(T-BINAP)(OCOCH$_3$)$_2$
Ru(T-BINAP)(OCOCF$_3$)$_2$
Ru(t-Bu-BINAP)(OCOCH$_3$)$_2$ In carrying out the present invention, a carbonyl compound of formula (II) is dissolved in an amphiprotic solvent, e.g., methanol, ethanol, methyl cellosolve, etc., or a mixed solvent of such an amphiprotic solvent with tetrahydrofuran, toluene, benzene, methylene chloride, etc. The solution is charged in an autoclave, and from 1/100 to 1/50,000 mol of a ruthenium-optically active phosphine complex is added thereto per mol of the substrate (carbonyl compound). The hydrogenation reaction is effected under stirring at a temperature of from 5° to 50° C., and preferably from 25° to 35° C., at a hydrogen pressure of from 5 to 40 kg/cm$^2$ for a period of from 1 to 48 hours. After completion of the reaction, the solvent is removed by distillation, and the residue is distilled under reduced pressure or subjected to silica gel column chromatography to thereby isolate the desired optically active alcohol of formula (I) in a substantially quantitative yield.

The present invention will now be illustrated in greater detail with reference to Reference Examples and Examples, but it should be understood that the present invention is not deemed to be limited thereto. In these examples, analytical instruments and conditions used for various analyses are as follows.

1) Gas Chromatography (GC)

SHIMADZU GC-9A, manufactured by Shimadzu Corporation

Column: PEG-20M Silica Capillary, 0.25 mm in diameter and 25 m in length, manufactured by Gasukuro Kogyo Inc.
Measurement Temperature: 100°–250° C. and increasing at a rate of 3° C./min.

2) High Performance Liquid Chromatography (HPLC)

Hitachi Liquid Chromatography-655A-11 manufactured by Hitachi, Ltd.
Column: YMC-Pack 003-3 SIL and 002-3 SIL, manufactured by Yamamura Kagaku Kenkyusho K. K.
Developing Solvent: diethyl ether:hexane 1:9; flow rate: 1 ml/min
Detector: UV Detector 655A (UV-254), manufactured by Hitachi, Ltd.

3) Optical Rotation

Polarimeter DIP-4, manufactured by Nippon Bunko Kogyo K. K.

4) $^1$H NMR Spectrum

JNM-GX400 (400 MHz), manufactured by JEOL Ltd. Internal Standard: tetramethylsilane 5) $^{31}$P NMR Spectrum JNM-GX400 (161 MHz) manufactured by JEOL Ltd. Chemical shift was determined by using 85% phosphoric acid as an external standard.

REFERENCE EXAMPLE 1

Synthesis of Ru$_2$Cl$_4$((+)-BINAP)$_2$(NEt$_3$) (di[2,2'-bis(diphenylphosphino)-1,1'-binaphthyl]tetrachloro-diruthenium triethylamine)

To 100 ml of toluene were added 1 g (3.56 mmols) of [RuCl$_2$(COD)]$_n$, 2.66 g (4.27 mmols) of (+)-BINAP, and 1.5 g of triethylamine in a nitrogen atmosphere, and the mixture was heat-refluxed for 10 hours. The solvent was removed from the reaction mixture by distillation under reduced pressure, and the residual solid was dissolved in methylene chloride, followed by filtration through Celite. The filtrate was concentrated to dryness to obtain 3.7 g of the entitled compound as a deep brown solid.

Elemental Analysis for C$_{94}$H$_{79}$Cl$_4$NP$_4$Ru$_2$:
Calcd (%): Ru 11.96; C 66.85; H 4.71; P 7.33.
Found (%): Ru 11.68; C 67.62; H 4.97; P 6.94.
$^1$H NMR (CDCl$_3$) δ ppm:
1.30–1.50 (t, 6H, NCH$_2$CH$_3$),
3.05–3.30 (q, 4H, NCH$_2$CH$_3$) and
6.40–8.60 (m, 32H, Ar-H)

REFERENCE EXAMPLE 2

Synthesis of [Ru((−)-T-BINAP)](ClO$_4$)$_2$ ([2,2'-bis(di-ptolylphosphino)-1,1'-binaphthyl]ruthenium perchlorate)

In a 250 ml-volume Schlenk's tube was charged 0.54 g (0.3 mmol) of Ru$_2$Cl$_4$((−)-T-BINAP)$_2$(NEt$_3$). After thorough displacement of the atmosphere with nitrogen gas, 60 ml of methylene chloride was added thereto, and then a solution of 0.73 g (6.0 mmols) of sodium perchlorate in 60 ml of water and a solution of 16 mg (0.06 mmol) of triethylbenzylammonium bromide in 3 ml of water were added to the mixture. The mixture was stirred at room temperature for 12 hours. After completion of the reaction, the reaction mixture was allowed to stand, and the aqueous layer was removed. The methylene chloride was removed from the organic layer by distillation under reduced pressure, and the residue was dried under reduced pressure to obtain 0.59 g (yield: 99.6%) of the entitled compound as a deep brown solid.

Elemental Analysis for $C_{48}H_{40}Cl_2O_8P_2Ru$:
Calcd. (%): Ru 10.32; C 58.90; H 4.12; P 6.33.
Found (%): Ru 10.08; C 58.61; H 4.53; P 5.97.
$^{31}P$ NMR ($CDCl_3$) δ ppm:
12.920 (d, J=41.1 Hz) and
61.402 (d, J=41.1 Hz)

REFERENCE EXAMPLE 3

Synthesis of Ru((−)-BINAP)(OCOCH$_3$)$_2$ ([2,2′-bis(diphenylphosphino)-1,1′-binaphthyl]ruthenium-diacetate)

In a 250 ml-volume Schlenk's tube were charged 1.43 g (0.85 mmol) of $Ru_2Cl_4((-)-BINAP)_2(NEt_3)$ and 3.06 g (37 mmols) of sodium acetate. After thorough displacement of the atmosphere with nitrogen, 100 ml of t-butanol was added to the mixture, followed by heating at reflux for 12 hours. After completion of the reaction, the t-butanol was removed by distillation under reduced pressure of 20 mmHg. The resulting solid was extracted twice with 10 ml of diethyl ether. The diethyl ether was distilled off from the extract, and the resulting solid was further extracted twice with 10 ml of ethanol. The extract was concentrated to dryness to obtain 1.50 g of crude Ru((−)-BINAP)(OCOCH$_3$)$_2$. Recrystallization of the crude product from ethyl acetate yielded 0.79 g (52%) of the entitled compound as a yellowish brown solid.

Melting Point: 180°–181° C. (with decomposition)
Elemental Analysis for $C_{48}H_{38}O_4P_2Ru$:
Calcd. (%): Ru 12.01; P 7.36; C 68.48; H 4.55.
Found (%): Ru 11.85; P 7.28; C 68.35; H 4.61.
$^{31}P$ NMR ($CDCl_3$) δ ppm:
65.00 (s)
$^1H$ NMR ($CDCl_3$) δ ppm: 1.75 (s, 6H,

)
and 6.5–7.8 (m, 32H, naphthyl ring and phenyl proton)

EXAMPLE 1

In a 200 ml-volume stainless steel-made autoclave whose atmosphere had been displaced with nitrogen were charged 0.87 ml (10 mmols) of diacetyl and 50 ml of methanol, and 42 mg (0.025 mmol) of $Ru_2Cl_4((+)-BINAP)_2(NEt_3)$ as prepared in Reference Example 1 was added thereto to effect hydrogenation at a temperature of 30° C. and a hydrogen pressure of 40 kg/cm$^2$ for 15 hours. The solvent was removed by distillation, and the residue was subjected to silica gel column chromatography using ethyl acetate as an eluent to remove the catalyst. There was obtained 0.84 g (yield: 95%) of 2,3-butanediol. The resulting alcohol was found to comprise 38% of a dl-compound [(2R, 3R)-compound] and 62% of a meso compound. The dl-compound had an optical rotation $[\alpha]_D^{25}$ of −13.2° (neat).

Thirty milligrams of the resulting alcohol was esterified with (+)-α-methoxy-α-trifluoromethylphenylacetyl chloride, and the ester was analyzed by HPLC to calculate a diasteromer ratio. As a result, it was found that the above-prepared alcohol had an optical purity of 99%ee.

EXAMPLE 2

In a 200 ml-volume autoclave whose atmosphere had been displaced with nitrogen were charged 7.7 g (100 mmols) of α-hydroxyacetone and 60 ml of methanol, and 168 ml (0.099 mmol) of $Ru_2Cl_4((+)-BINAP)_2(NEt_3)$ as prepared in Reference Example 1 was added thereto to effect hydrogenation at a temperature of 30° C. and a hydrogen pressure of 30 kg/cm$^2$ for 20 hours. After the reaction, the solvent was removed by distillation to obtain 1,2-propanediol having a boiling point of 121° to 122° C./5 mmHg. The optical rotation $[\alpha]_D^{25}$ of the resulting alcohol was −15.3° (neat). The product was esterified with (+)-α-methoxy-α-trifluoromethylphenylacetyl chloride to obtain a diastereomer. As a result of HPLC of the diastereomer, the optical purity of the above-prepared alcohol was found to be 99%ee.

EXAMPLE 3

In a 200 ml-volume autoclave whose atmosphere had been displaced with nitrogen were charged 11.5 g (0.1 mol) of 3-methyl-2-oxobutanoic acid and 100 ml of toluene, and 88 mg (0.090 mmol) of [Ru((−)-T-BINAP)](ClO$_4$)$_2$ as prepared in Reference Example 2 was added thereto to effect hydrogenation at a temperature of 60° C. and a hydrogen pressure of 50 kg/cm$^2$ for 20 hours. After completion of the reaction, the solvent was removed by distillation, and the residue was extracted with an alkali. The aqueous layer was neutralized and extracted with diethyl ether. The extract was concentrated and dried to obtain 8 g of (R)-3-methyl-2-hydroxybutanoic acid having a melting point of 63° to 65° C. The optical rotation $[\alpha]_D^{25}$ of the resulting alcohol was +10.65° ($CHCl_3$). In the light of the optical rotation available in the literature, $[\alpha]_D^{25}=+16.9°$ ($CHCl_3$), the optical purity of the product was found to be 63%ee.

EXAMPLE 4

In a 200 ml-volume autoclave whose atmosphere had been displaced with nitrogen were charged 10 g (0.1 mol) of α-(N,N-dimethyl)aminoacetone, 50 ml of methanol, and 10 ml of methylene chloride. Then, 84 mg (0.10 mmol) of Ru((−)-BINAP)(OCOCH$_3$)$_2$ as prepared in Reference Example 3 was added thereto to effect hydrogenation at a temperature of 30° C. and a hydrogen pressure of 60 kg/cm$^2$ for 20 hours. After the reaction, the solvent was distilled off to obtain 9 g of D-(−)-1-(N,N-dimethylamino)-2-propanol having an optical rotation $[\alpha]_D^{25}$ of −20.7° C. (C=0.83, $CH_3OH$).

The resulting alcohol was led to an ester with (+)-α-methoxy-α-trifluoromethylphenylacetyl chloride, and the ester was subjected to HPLC to calculate a diastereomer ratio. As a result, it was found that the above-prepared alcohol had an optical purity of 91%ee.

EXAMPLES 5 TO 34

The same procedure of Example 1 was repeated, except for altering the substrate, catalyst and reaction conditions as shown Table 1 below. The analytical results obtained are shown in Table 1.

TABLE 1

| Example No. | Substrate | Catalyst | Reaction Condition | | | | | Product | Yield (%) | Optical Yield (% ee) |
|---|---|---|---|---|---|---|---|---|---|---|
| | | | Substrate/Catalyst (mol/mol) | Solvent | Hydrogen Pressure (kg/cm²) | Temperature (°C.) | Time (hr) | | | |
| 5 | $CH_3-\overset{O}{\overset{\|}{C}}-\overset{O}{\overset{\|}{C}}-CH_3$ | $Ru_2Cl_4((-)-T-BINAP)_2-(NEt_3)$ | 100 | methanol:methylene chloride (5:1) | 40 | 30 | 15 | $CH_3-\overset{OH}{\overset{\|}{CH}}-\overset{OH}{\overset{\|}{CH}}-CH_3$ | 97 | 99 |
| 6 | Ph-CO-CO-Ph | $Ru_2Cl_4((-)-T-BINAP)_2-(NEt_3)$ | 100 | methanol:methylene chloride (5:1) | 40 | 35 | 20 | Ph-CH(OH)-CH(OH)-Ph | 87 | 92 |
| 7 | cyclopentane-1,2-dione | $Ru_2Cl_4((-)-t-Bu-BINAP)_2(NEt_3)$ | 100 | methanol | 35 | 30 | 17 | trans-1,2-cyclopentanediol | 91.5 | 94.2 |
| 8 | cyclohexane-1,2-dione | $Ru_2Cl_4((+)-BINAP)_2-(NEt_3)$ | 100 | methanol:methylene chloride (5:1) | 45 | 35 | 15 | trans-1,2-cyclohexanediol | 93.1 | 95.3 |
| 9 | Ph-CO-CO₂H | $Ru((+)-BINAP)(O_2CCH_3)_2$ | 80 | toluene | 50 | 60 | 20 | Ph-CH(OH)-CO₂H | 93 | 45 |
| 10 | $(CH_3)_2CH-\overset{O}{\overset{\|}{C}}-CO_2H$ | $[Ru((-)-T-BINAP)]-(ClO_4)_2$ | 100 | toluene | 45 | 60 | 20 | $(CH_3)_2CH-\overset{OH}{\overset{\|}{CH}}-CO_2H$ | 95 | 35 |
| 11 | $(CH_3)_2CH-\overset{O}{\overset{\|}{C}}-CO_2H$ | $[RuH((-)-T-BINAP)]-ClO_4$ | 100 | toluene | 35 | 65 | 18 | $(CH_3)_2CH-\overset{OH}{\overset{\|}{CH}}-CO_2H$ | 95 | 32 |
| 12 | Ph-CO-CO₂C₂H₅ | $Ru_2Cl_4((-)-T-BINAP)_2-(NEt_3)$ | 100 | ethanol | 35 | 30 | 24 | Ph-CH(OH)-CO₂C₂H₅ | 97.5 | 91.4 |
| 13 | $(CH_3)_2CH-\overset{O}{\overset{\|}{C}}-CO_2C_2H_5$ | $Ru_2Cl_4((-)-BINAP)_2-(NEt_3)$ | 100 | ethanol | 40 | 35 | 18 | $(CH_3)_2CH-\overset{OH}{\overset{\|}{CH}}-CO_2C_2H_5$ | 96 | 92.5 |

TABLE 1-continued

| Example No. | Substrate | Catalyst | Substrate/Catalyst (mol/mol) | Solvent | Hydrogen Pressure (kg/cm²) | Temperature (°C.) | Time (hr) | Product | Yield (%) | Optical Yield (% ee) |
|---|---|---|---|---|---|---|---|---|---|---|
| 14 | (lactone with ketone) | Ru₂Cl₄((−)-T—BINAP)₂—(NEt₃) | 100 | methanol | 35 | 35 | 15 | (lactone with OH) | 95.5 | 90.7 |
| 15 | C₆H₅—CO—CH₃ | Ru₂Cl₄((−)-t-Bu—BINAP)₂(NEt₃) | 75 | methanol | 50 | 30 | 20 | C₆H₅—CH(OH)—CH₃ | 90 | 95 |
| 16 | C₆H₅—CH₂—CO—CO—CH₃ | Ru₂Cl₄((+)-BINAP)₂—(NEt₃) | 100 | methanol | 40 | 30 | 15 | C₆H₅—CH₂—CH(OH)—CH(OH)—CH₃ | 95 | 96.3 |
| 17 | C₆H₅—CH₂—CO—CO₂H | Ru((−)-T—BINAP)—(O₂CCH₃)₂ | 300 | toluene | 35 | 40 | 18 | C₆H₅—CH₂—CH(OH)—CO₂H | 89 | 40 |
| 18 | C₆H₅—CH₂—CO—CO₂C₂H₅ | Ru₂Cl₄((−)-t-Bu—BINAP)₂(NEt₃) | 100 | methanol | 40 | 35 | 15 | C₆H₅—CH₂—CH(OH)—CO₂C₂H₅ | 75 | 88 |
| 19 | CH₃—CO—CO₂H | [Ru((+)-BINAP)]—(ClO₄)₂ | 100 | methanol | 35 | 35 | 18 | CH₃—CH(OH)—CO₂H | 93 | 33 |
| 20 | CH₃—CO—CH₂Cl | Ru₂Cl₄((−)-t-Bu—BINAP)₂(NEt₃) | 50 | methanol | 40 | 30 | 17 | CH₃—CH(OH)—CH₂Cl | 96 | 91 |
| 21 | CH₃—CO—CH₂Br | Ru₂Cl₄((+)-BINAP)₂—(NEt₃) | 100 | methanol | 40 | 35 | 18 | CH₃—CH(OH)—CH₂Br | 75 | 85 |
| 22 | (CH₃)₂CH—CO—CH₂Cl | Ru₂Cl₄((−)-t-Bu—BINAP)₂(NEt₃) | 100 | methanol | 50 | 30 | 15 | (CH₃)₂CH—CH(OH)—CH₂Cl | 95 | 88 |

TABLE 1-continued

| Example No. | Substrate | Reaction Condition | | | | | | Product | Yield (%) | Optical Yield (% ee) |
|---|---|---|---|---|---|---|---|---|---|---|
| | | Catalyst | Substrate/ Catalyst (mol/mol) | Solvent | Hydrogen Pressure (kg/cm²) | Temperature (°C.) | Time (hr) | | | |
| 23 | C₆H₅–CO–CH₂–C(O)–CH₂Cl | [RuH((+)-BINAP)₂]PF₆ | 50 | methanol | 80 | 35 | 25 | C₆H₅–CH(OH)–CH₂–CH(OH)–CH₂Cl | 95 | 88 |
| 24 | CH₃–C(O)–CHCl₂ | [Ru((−)-T-BINAP)](PF₆)₂ | 35 | ethanol | 70 | 30 | 48 | CH₃–CH(OH)–CHCl₂ | 65 | 85 |
| 25 | CH₃–C(O)–CH₂NHCH₃ | Ru((−)-BINAP)(OCOCH₃)₂ | 100 | methanol | 50 | 35 | 20 | CH₃–CH(OH)–CH₂NHCH₃ | 85 | 89 |
| 26 | CH₃–C(O)–CH₂N(CH₃)₂ | Ru((−)-T-BINAP)(OCOCF₃)₂ | 100 | methanol | 40 | 20 | 20 | CH₃–CH(OH)–CH₂N(CH₃)₂ | 95 | 91 |
| 27 | C₆H₅–C(O)–CH₂OH | [Ru((−)-t-Bu–BINAP)](ClO₄)₂ | 100 | methanol | 40 | 30 | 24 | C₆H₅–CH(OH)–CH₂OH | 90 | 63 |
| 28 | (CH₃)₂CH–C(O)–CH₂OH | Ru₂Cl₄((−)-T-BINAP)₂(NEt₃) | 150 | methanol | 50 | 30 | 40 | (CH₃)₂CH–CH(OH)–CH₂OH | 96 | 93 |
| 29 | C₆H₅–C(O)–CH₂OH | Ru₂Cl₄((−)-BINAP)₂(NEt₃) | 100 | methanol | 50 | 30 | 30 | C₆H₅–CH(OH)–CH₂OH | 90 | 89 |
| 30 | CH₃–C(O)–CH₂OCH₃ | Ru₂Cl₄((−)-T-BINAP)₂(NEt₃) | 150 | methanol | 50 | 30 | 48 | CH₃–CH(OH)–CH₂OCH₃ | 94 | 88 |
| 31 | C₆H₅–C(O)–CH₂OCH₃ | Ru₂Cl₄((+)-t-Bu–BINAP)₂(NEt₃) | 100 | methanol | 50 | 30 | 18 | C₆H₅–CH(OH)–CH₂OCH₃ | 93 | 87 |

TABLE 1-continued

| Example No. | Substrate | Catalyst | Substrate/Catalyst (mol/mol) | Solvent | Hydrogen Pressure (kg/cm²) | Temperature (°C.) | Time (hr) | Product | Yield (%) | Optical Yield (% ee) |
|---|---|---|---|---|---|---|---|---|---|---|
| 32 | (2-Cl-C₆H₄)-CO-CH₃ | Ru₂Cl₄((−)-BINAP)₂—(NEt₃) | 100 | methanol | 40 | 25 | 16 | (2-Br-C₆H₄)-CH(OH)-CH₃ | 95 | 82 |
| 33 | (2-Br-C₆H₄)-CO-CH₃ | Ru₂Cl₄((+)-BINAP)₂—(NEt₃) | 100 | methanol | 40 | 25 | 12 | (2-Cl-C₆H₄)-CH(OH)-CH₃ | 96 | 96 |
| 34 | C₆H₅-CO-CH₂N(CH₃)₂ | Ru((−)-BINAP)—(OCOCH₃)₂ | 100 | methanol | 100 | 25 | 18 | C₆H₅-CH(OH)-CH₂N(CH₃)₂ | 92 | 93 |

As described above, the present invention provides an industrially valuable process for preparing a useful optically active alcohol at high efficiency by asymmetric hydrogenation of a carbonyl compound.

While the invention has been described in detail and with reference to specific embodiments thereof, it will be apparent to on skilled in the art that various changes and modifications can be made therein without departing from the spirit and scope thereof.

What is claimed is:

1. A process for preparing an optically active alcohol represented by formula (I):

(I)

wherein A represents a lower alkyl group, phenyl or benzyl and B represents a lower alkoxycarbonyl group, a haloalkyl group, a lower alkoxyalkyl group, a hydroxymethyl group, a halophenyl group, or a lower alkyl-substituted aminomethyl group, provided that A and B cannot be the same simultaneously, which comprises asymmetrically hydrogenating a carbonyl compound represented by formula (II):

(II)

wherein A and B are as defined above, in the presence of a ruthenium-optically active phosphine complex as a catalyst.

2. A process as claimed in claim 1, wherein said ruthenium-optically active phosphine complex is selected from a compound represented by formula (V):

[RuH$_l$(R-BINAP)$_v$]Y$_w$   (V)

wherein R-BINAP represents a tertiary phosphine represented by formula (IV):

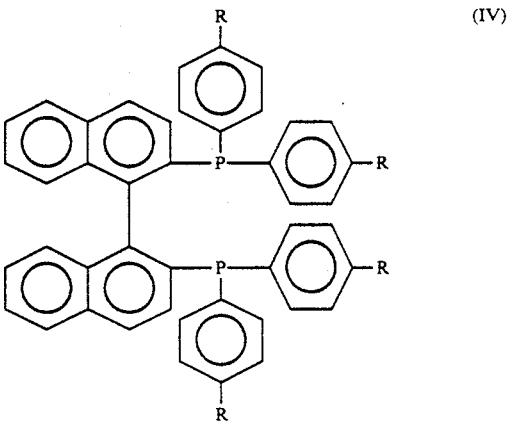
(IV)

wherein R represents a hydrogen atoms, a methyl group, or a t-butyl group; Y represents ClO$_4$, BF$_4$, or PF$_6$; when l represents 0, then v represents 1, and w represents 2; and when l represents 1, then v represents 2, and w represents 1, and a compound represented by formula (VI):

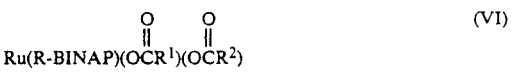
Ru(R-BINAP)(OCR$^1$)(OCR$^2$)   (VI)

wherein R-BINAP is as defined above; and R$^1$ and R$^2$ each represents a lower alkyl group or a trifluoromethyl group.

* * * * *